(12) United States Patent
Rivaz et al.

(10) Patent No.: US 8,559,685 B2
(45) Date of Patent: Oct. 15, 2013

(54) ROBUST AND ACCURATE FREEHAND 3D ULTRASOUND

(75) Inventors: Hassan Rivaz, Baltimore, MD (US); Emad Moussa Boctor, Baltimore, MD (US); Gabor Fichtinger, Kingston (CA); Gregory Hager, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 771 days.

(21) Appl. No.: 12/449,582

(22) PCT Filed: Feb. 19, 2008

(86) PCT No.: PCT/US2008/002116
§ 371 (c)(1),
(2), (4) Date: Apr. 7, 2010

(87) PCT Pub. No.: WO2008/100623
PCT Pub. Date: Aug. 21, 2008

(65) Prior Publication Data
US 2010/0198068 A1    Aug. 5, 2010

Related U.S. Application Data

(60) Provisional application No. 60/901,873, filed on Feb. 16, 2007.

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| | | | |
|---|---|---|---|
| 7,901,357 B2* | 3/2011 | Boctor et al. | 600/443 |
| 2002/0120195 A1* | 8/2002 | Hossack et al. | 600/443 |
| 2003/0018442 A1 | 1/2003 | Yamaguchi et al. | |
| 2005/0101865 A1 | 5/2005 | Hao et al. | |
| 2005/0187473 A1* | 8/2005 | Boctor et al. | 600/437 |
| 2006/0229744 A1 | 10/2006 | Patzwald et al. | |
| 2010/0198068 A1* | 8/2010 | Rivaz et al. | 600/443 |

OTHER PUBLICATIONS

A. H. Gee, R. J. Housden, P. Hassenpflug, G. M. Treece, and R. W. Prager. Sensorless freehand 3D ultrasound in real tissue: speckle decorrelation without fully developed speckle. Medical Image Analysis, Jan. 2005, pp. 1-19.*

Housden et al., Sub-sample Interpolation Strategies for Sensorless Freehand 3D Ultrasound, Ultrasound Med. Biology Jan. 2006, vol. 32(12); 1897-904.*

(Continued)

*Primary Examiner* — Bhavesh Mehta
*Assistant Examiner* — Tahmina Ansari
(74) *Attorney, Agent, or Firm* — Venable LLP; Henry J. Daley

(57) ABSTRACT

Disclosed is a system and method for computing out of plane motion between two ultrasound images. The method identifies regions of fully developed speckle that are common to the two images, computes a correlation coefficient corresponding to the two fully developed speckle image regions, and then computing an elevation distance corresponding to the correlation coefficient. The method exploits the measurable and characterizable relation between inter-image correlation and elevation distance, which may be determined from fully developed speckle regions. The method also identifies regions within the ultrasound images related to structure (e.g., vein or bone), and disregards these regions.

20 Claims, 13 Drawing Sheets

(56) References Cited

OTHER PUBLICATIONS

Rivaz, H. et al., "Real-Time Regularized Ultrasound Elastography" Medical Imaging, IEEE Transactions on vol. 30, Issue: 4 Publication Year: 2011, pp. 928-945 Digital Object Identifier: 10.1109/TMI.2010.2091966.*

Azar, A.A. et al. "Speckle detection in ultrasonic images using unsupervised clustering techniques", Engineering in Medicine and Biology Society,EMBC, 2011 Annual International Conference of the IEEE, Publication Year: 2011, pp. 8098-8101, Digital Object Identifier: 10.1109/IEMBS.2011.6091997.*

Housden et al., "Sub-sample Interpolation Strategies for Sensorless Freehand 3D Ultrasound," Ultrasound Med. Biol 2006, vol. 32(12); 1897-904, Retrived from the Internet Jul. 3, 2008, http://mi.eng.cam.ac.uk/reports/svr-ftp/housden_tr545.pdf, pp. 1-11.

* cited by examiner

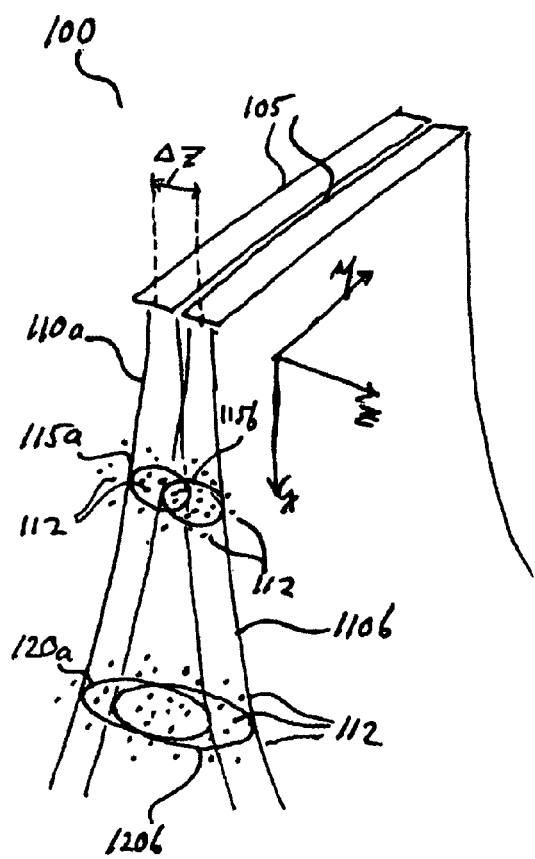
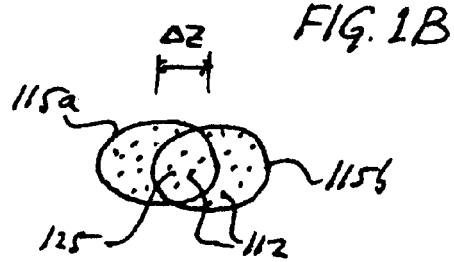
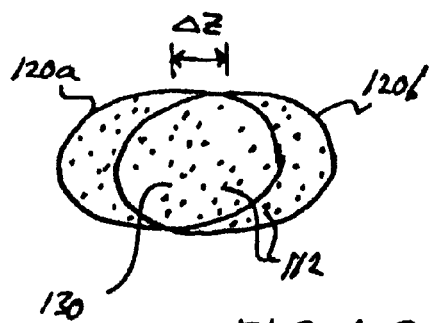
FIG. 1A
FIG. 1B
FIG. 1C

US 8,559,685 B2

ROBUST AND ACCURATE FREEHAND 3D ULTRASOUND

This application claims the benefit of PCT Application No. PCT/US2008/002116, filed on Feb. 19, 2008 and U.S. Provisional Patent Application No. 60/901,873, filed on Feb. 16, 2007, which is hereby incorporated by reference for all purposes as if fully set forth herein.

BACKGROUND

1. Field of the Invention

The present invention generally relates to ultrasound imaging. More particularly, the application relates to the generation of 3D images using ultrasound.

2. Discussion of the Related Art

Ultrasound imaging has become a widely used medical imaging modality, due in part to its effectiveness in safely imaging tissue, its ease of use, and lower cost. Ultrasound has become an essential imaging tool in applications such as identifying tissue anomalies, monitoring fetal development, and assisting in guiding surgical devices in invasive treatments.

Considerable effort has recently been devoted to generating 3D images from multiple ultrasound images. By acquiring multiple images of a tissue region of interest, from multiple angles and positions, it is possible to merge the multiple images to generate a 3D image. Approaches to accomplishing this have included (a) precisely measuring the position and orientation of the ultrasound probe for each image acquired; and/or (b) identifying common tissue features across multiple images to serve as markers for registering the plurality of images into a single 3D image space.

Precisely measuring the position and orientation of the ultrasound probe generally requires additional equipment, which is expensive, and complicates the use of the ultrasound probe. For example, one related art approach involves attaching the ultrasound probe to a robotic arm, which precisely controls the position and orientation of the ultrasound probe. Another related art approach involves mounting optical tracking devices to a handheld ultrasound probe. The latter approach requires equipping the room with optical scanning devices, which is expensive to implement and restricts the use of the ultrasound probe to the room in which the optical scanning devices are installed. Further, line-of-sight between the optical scanning devices and the optical tracking devices (mounted on the ultrasound probe) must be maintained in order for the position and orientation of the ultrasound probe to be computed. Both of these related art solutions add considerable cost and complexity to an ultrasound system.

As mentioned above, another approach involves identifying tissue features common to multiple images for registering multiple ultrasound images to a single 3D image space. This is typically done by inferring the relative position and orientation of the ultrasound probe by determining the location of the common tissue features in each ultrasound image. This is generally easier if the ultrasound probe's motion is constrained to the ultrasound image plane, so that the same common features appear in each ultrasound image. In this case, it is generally easy to compute the translation and rotation of the ultrasound probe by computing the displacement of the tissue features between images. However, this is not so simple in the case of out of plane motion. Out of plane motion is that in which the ultrasound probe translates and/or rotates so that tissue features move with a vector component perpendicular to the ultrasound image plane. In this case, tissue features, which are typically required to register one image to another, disappear due to motion of the ultrasound probe.

Accordingly, what is needed is a system and method for registering multiple ultrasound images into a single 3D image space, without the expense and complication of additional control/measurement hardware, and which addresses the problem of out of plane motion.

SUMMARY OF THE INVENTION

The present invention provides a method for robust and accurate 3D ultrasound that obviates one or more of the aforementioned problems due to the limitations of the related art.

Accordingly, one advantage of the present invention is that it improves ultrasound probe calibration for 3D ultrasound imaging.

Another advantage of the present invention is that it provides for more robust ultrasound image registration.

Another advantage of the present invention is that it better provides for ultrasound image-guided surgical interventions.

Still another advantage of the present invention is that it improves out of plane motion tracking of ultrasound speckle features.

Additional advantages of the invention will be set forth in the description that follows, and in part will be apparent from the description, or may be learned by practice of the invention. The advantages of the invention will be realized and attained by the structure pointed out in the written description and claims hereof as well as the appended drawings To achieve these and other advantages, the present invention involves a method for generating 3D ultrasound imagery. The method comprises acquiring a first ultrasound image and a second ultrasound image, the first ultrasound image corresponding to a first image location, and second ultrasound image corresponding to a second image location, and wherein the first image location and the second image location are separated by an elevation distance; dividing the first ultrasound image and the second ultrasound image into a plurality of patches; computing a signal to noise ratio value and a skewness value for each of the plurality of patches; comparing the signal to noise ratio value and skewness value for each patch to a range of acceptable signal to noise ratio values and a range of acceptable skewness values; determining if there is a plurality of good patches, wherein the good patches have a corresponding signal to noise ratio value and skewness value that lie within the range of acceptable signal to noise ratio values and skewness values; if it is determined that there is a plurality of good patched, computing a correlation coefficient for a corresponding pair of good patches, wherein one of the corresponding pair is from the first ultrasound image, and the other of the corresponding pair is from the second ultrasound image; if it is determined that there is a plurality of good patches, computing an elevation distance corresponding to the correlation coefficient; and constructing a 3D image using the first and second ultrasound images and the elevation distance.

In another aspect of the present invention, the aforementioned and other advantages are achieved by a method for determining out of plane motion between a first ultrasound image and a second ultrasound image, which comprises dividing the first ultrasound image into a first plurality of patches, wherein each of the first plurality of patches has a first plurality of pixel data; dividing the second ultrasound image into a second plurality of patches, wherein each of the second plurality of patches has a second plurality of pixel data; combining one of the first plurality of pixel data with a corresponding one of the second pixel data; computing a signal to noise ratio value and a skewness value corresponding to the combined pixel data; comparing the signal to noise ratio value and skewness value with a range of acceptable signal to noise ratio values and skewness values; depending on a result of the comparing, computing a correlation coefficient corresponding to the one of one of the first plurality of pixel data with the corresponding one of the second pixel data; computing an elevation distance corresponding to the correlation coefficient and constructing a 3D image using the first ultrasound image, the second ultrasound image, and the elevation distance.

In another aspect of the present invention, the aforementioned and other advantages are achieved by a system for generating 3D ultrasound images. The system comprises an ultrasound probe; a processor coupled to the ultrasound probe; and a memory coupled to the processor, wherein the memory is encoded with instructions for acquiring a first ultrasound image and a second ultrasound image, the first ultrasound image corresponding to a first image location, and second ultrasound image corresponding to a second image location, and wherein the first image location and the second image location are separated by an elevation distance; dividing the first ultrasound image and the second ultrasound image into a plurality of patches; computing a signal to noise ratio value and a skewness value for each of the plurality of patches; comparing the signal to noise ratio value and skewness value for each patch to a range of acceptable signal to noise ratio values and a range of acceptable skewness values; determining if there is a plurality of good patches, wherein the good patches have a corresponding signal to noise ratio value and skewness value that lie within the range of acceptable signal to noise ratio values and skewness values; if it is determined that there is a plurality of good patched, computing a correlation coefficient for a corresponding pair of good patches, wherein one of the corresponding pair is from the first ultrasound image, and the other of the corresponding pair is from the second ultrasound image; and if it is determined that there is a plurality of good patches, computing an elevation distance corresponding to the correlation coefficient.

In yet another aspect of the present invention, the aforementioned and other advantages are achieved by a system for generating 3D ultrasound images. The system comprises an ultrasound probe; a processor coupled to the ultrasound probe; and a memory coupled to the processor, wherein the memory is encoded with instructions for acquiring a first ultrasound image and a second ultrasound image; dividing the first ultrasound image into a first plurality of patches, wherein each of the first plurality of patches has a first plurality of pixel data; dividing the second ultrasound image into a second plurality of patches, wherein each of the second plurality of patches has a second plurality of pixel data; combining one of the first plurality of pixel data with a corresponding one of the second pixel data; computing a signal to noise ratio value and a skewness value corresponding to the combined pixel data; comparing the signal to noise ratio value and skewness value with a range of acceptable signal to noise ratio values and skewness values; depending on a result of the comparing, computing a correlation coefficient corresponding to the one of one of the first plurality of pixel data with the corresponding one of the second pixel data; computing an elevation distance corresponding to the correlation coefficient, and constructing a 3D image using the first ultrasound image, the second ultrasound image, and the elevation distance.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 1A illustrates two exemplary ultrasound probe fields of view, in which the fields of view are separated by an out of plane motion;

FIG. 1B illustrates two overlapping resolution cells that are relatively close to the ultrasound probe, or in a shallow region of the tissue medium;

FIG. 1C illustrates two overlapping resolution cells that are relatively far from the ultrasound probe, or in a deep region of the tissue medium;

DETAILED DESCRIPTION

Figure 2:
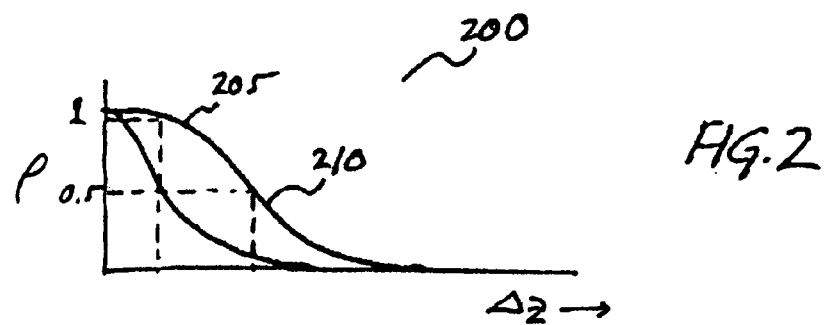
FIG. 2 illustrates an exemplary correlation curve set.

The system and method described herein exploits the traits of Fully Developed Speckle (FDS) in ultrasound imagers, whereby the extent of correlation between two images of a single FDS feature falls off at a measurable and characterizable rate as a function of out of plane distance, and as a function of depth within the ultrasound image.

FIG. 1A illustrates an ultrasound probe 100 acquiring two successive images while being scanned in an out of plane direction. Probe 100 has a transducer array 105, which is depicted at two sequential scan positions. Transducer array 105 has a first field of view 110a, corresponding to a first scan position, and a second field of view 110b, corresponding to a second scan position. First field of view 110a has a shallow resolution cell 115a and a deep resolution cell 120a. Shallow resolution cell 115a is a volume within field of view 110a that corresponds to the field of view of a single transducer for a given sample integration time. The timing of the sample integration time is such that shallow resolution cell 115a is a specific distance from transducer array 105, which is closer to transducer array 105 than deep resolution cell 120a. Deep resolution cell 120a has a volume defined by the field of view of the same transducer as 115a, but a sample integration time such that the sample is acquired further from transducer array 105, i.e., deeper into the tissue than shallow resolution cell 115a.

FIG. 1A also illustrates an ultrasound image coordinate space, having an axial direction (x-axis), a lateral direction (y-axis), and an elevation direction (z-axis, also referred to the out of plane direction). As illustrated, second field of view 110b is offset from first field of view 110a by a translation ($\Delta z$, also referred to as "elevation distance") along the elevation direction, or z-axis. Further, as illustrated, both fields of view 110a and 110b have substantially similar geometry such that the y and z dimensions of the resolution cells within a given field of view increase as a function of distance along the x direction.

Further although FIG. 1A only illustrates resolution cells at two different depths (deep and shallow), one skilled in the art will readily recognize that these resolution cells are examples of a plurality of resolution cells that propagate along the x direction, such that the y and z dimensions of a resolution cell may be dictated by the geometry of transducer array 105, the acoustic properties of the tissue medium, and the distance along the x axis, and that the x dimension of a given resolution cell is a function of the sample integration time employed by ultrasound probe 100.

FIG. 1A further illustrates a plurality of speckle scatterers 112 that are distributed throughout the tissue medium. As illustrated, speckle scatterers 112 are distributed throughout the shallow resolution cells 115a and 115b, and deep resolution cells 120a and 120b.

FIG. 1B illustrates shallow resolutions cells 115a and 115b, as viewed along the x axis. Shallow resolution cells 115a and 115b have an overlap region 125, the area of which is determined by the areas of shallow resolution cells 115a and 115b, and elevation distance $\Delta z$. Further illustrated are speckle scatterers 112, distributed throughout shallow resolution cells 115a and 115b, including overlap region 125.

FIG. 1C illustrates deep resolution cells 120a and 120b, as viewed along the x axis. Deep resolution cells 120a and 120b have an overlap region 130, the area of which is determined by the areas of deep resolution cells 120a and 120b, and elevation distance $\Delta z$. Further illustrated are speckle scatterers 112, distributed throughout deep resolution cells 120a and 120b, including overlap region 130.

As illustrated in FIGS. 1B and 1C, the ratio of the area of overlap region 130 to the area of deep resolution cell 120a or 120b is greater than the ratio of the area of overlap region 125 to the area of shallow resolution cell 115a or 115b. This is due to the fact that the area of a resolution cell within an ultrasound field of view gets larger as a function of distance along the axial or x direction, and that the elevation distance $\Delta z$ remains substantially constant (given that fields of view 110a and 110b are spatially offset by a translation with little or no rotation).

Given the increase in overlap region in proportion to resolution cell area as a function of axial distance, a higher percentage of speckle scatterers 112 are common to deep resolution cells 120a and 120b, as compared to shallow resolution cells 115a and 115b. The result of this is that, in imaging a substantially uniform tissue medium, there will be a higher correlation in ultrasound signals between two deep resolution cells 120a and 120b, relative to shallow resolution cells 115a and 115b. Further, that the correlation between ultrasound signals for shallow and deep resolution cells 115a/115b and 120a/120b diminishes as a function of elevation distance $\Delta z$.

FIG. 2 illustrates an exemplary correlation curve set 200 for two resolution cells corresponding to two different tissue depths. Correlation curve 205 corresponds the correlation between to two shallow resolution cells 115a and 115b, as a function of elevation distance $\Delta z$. And correlation curve 210 corresponds to the correlation between two deep resolution cells 120a and 120b, as a function of elevation distance $\Delta z$. As illustrated, for both curves 205 and 210, given a substantially isotropic tissue medium, with a distribution of a sufficient number of speckle scatters 112, the correlation coefficient ρ may behave as a function of elevation distance $\Delta z$ according to a Rayleigh distribution. In order for correlation curve 205 or 210 to have a Rayleigh distribution, there must be at least 10 speckle scatterers 112 within overlap region 125 and 130.

As used herein, Fully Developed Speckle (FDS) may refer to a density and distribution of speckle scatterers 112 such that there are at least 10 speckle scatterers 112 within overlapping regions of corresponding resolution cells.

As illustrated in FIG. 2, a correlation ρ of 0.5 (for example), corresponds to a greater elevation distance $\Delta z$ for deeper resolution cells than for shallower resolution cells. Conversely, for a given elevation distance $\Delta z$, the correlation ρ is greater for deeper resolution cells than for shallower resolution cells. Accordingly, if one knows the depth (along the axial or x direction) of a given resolution cell, and if one can compute a correlation between two overlapping resolution cells at that depth, one may use correlation curve set 200 to determine the elevation distance $\Delta z$ between corresponding resolution cells of two fields of view.

However, this is generally difficult because tissue medium is rarely isotropic within two fields of view, such as first field of view 110a and second field of view 110b. The presence of structure within the tissue medium, such as veins, bone, and the like, create correlations between overlapping resolution cells that do not diminish as a function of elevation distance $\Delta z$, as is the case with FDS. In other words, the persistent correlation induced by structure within a tissue interferes with the ability to exploit FDS to determine elevation distance $\Delta z$ as a function of correlation.

Figure 3:
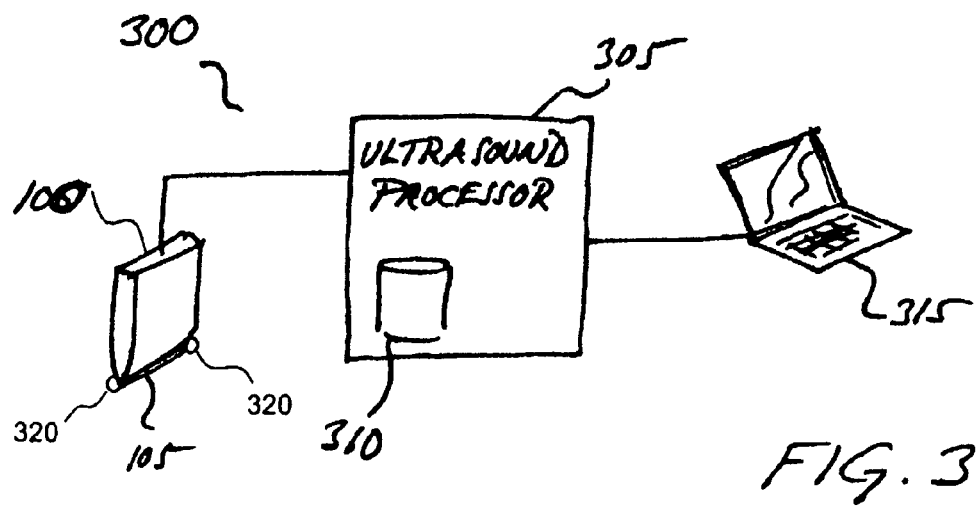
FIG. 3 illustrates an exemplary system for freehand ultrasound 3D imaging.

FIG. 3 illustrates an exemplary system 300 for generating 3D ultrasound images. System 300 may include an ultrasound probe 100, and ultrasound processor 305 having a memory device 310, and a user interface 315. All of the components of system 300 may be parts of an existing commercial ultrasound system, with memory device 310 having additional machine readable instructions for performing processes disclosed herein. Alternatively, ultrasound processor 305 may be a separate computer or computer system, which receives ultrasound image data from a separate standalone ultrasound system.

Further, system 300 may also include one or more additional motion sensors 320. Additional motion sensors 320 may include, for example, an optical tracking device similar to the LED or image correlation-based tracking used in a computer mouse. In this example, additional sensors 320 (optical tracking devices) may be placed on either side of transducer array 105. As an ultrasound technician moves ultrasound probe 100 over a patient's anatomy, the optical tracking devices detect the direction and displacement over the patient's skin. By using two optical tracking sensors, additional two degree of freedom motion information between first field of view 110a and 110b may be obtained. Ultrasound processor 305 may execute instructions to acquire the motion data from the optical tracking sensors, compute a two degree of freedom solution for motion between fields of view 110a and 110b, and store this information in memory 310. Alternatively (or additionally) additional sensors 320 may include other types of motion sensors, such as accelerometers, and the like. One skilled in the art will readily appreciate that such variations to additional sensors 320 (and to system 300) are possible and within the scope of the invention.

Memory device 310 may include one or more computer readable storage media. Memory device 310 may include multiple storage devices that are accesses over a network. One skilled in the art will readily appreciate that many variations to system 300 are possible and within the scope of the invention.

Figure 4:
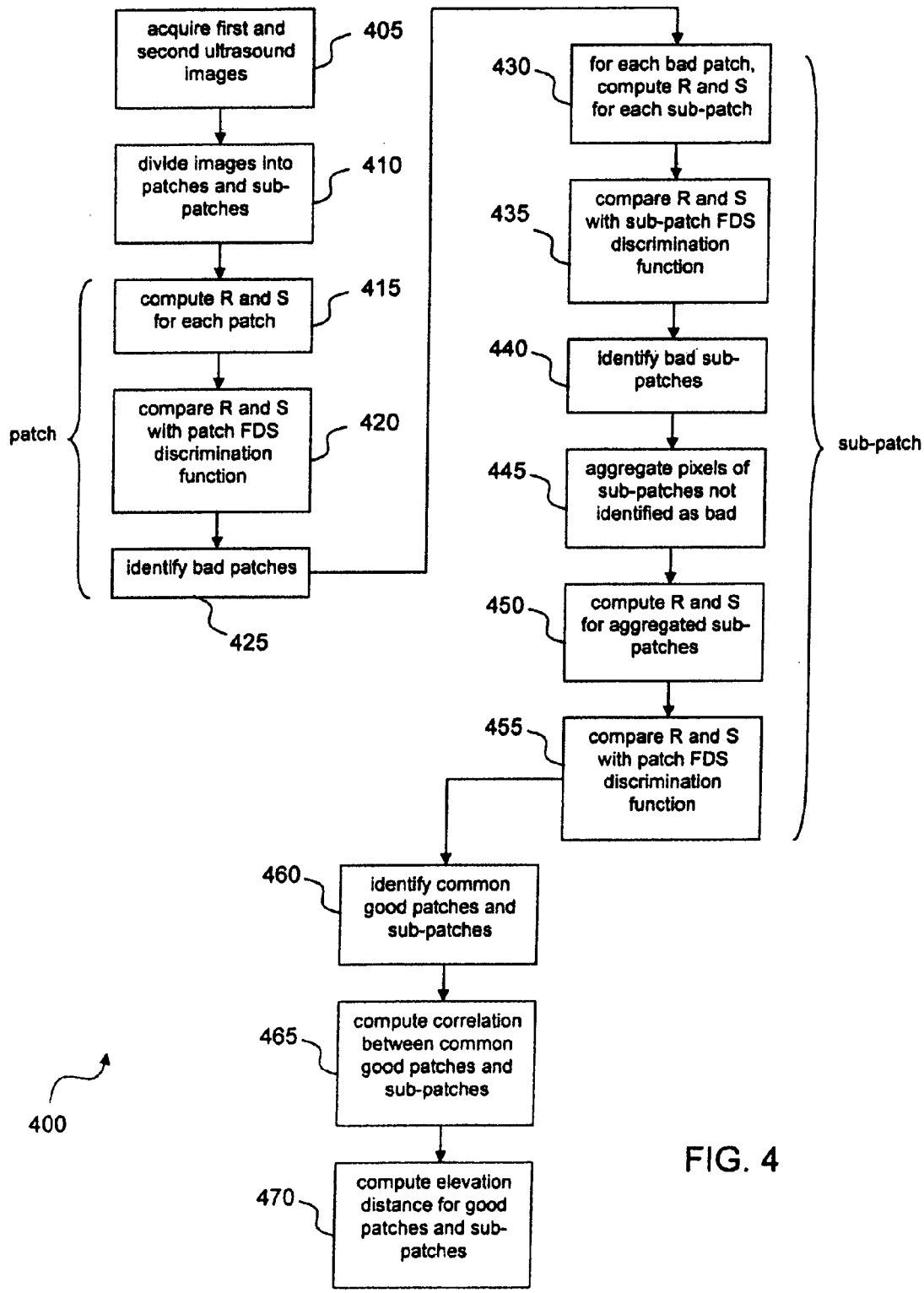
FIG. 4 illustrates an exemplary process for freehand ultrasound 3D imaging.

FIG. 4 illustrates an exemplary process 400 for generating 3D ultrasound images. Process 400 may be performed by the processor(s) within system 300. All of the processes disclosed herein may be implemented as machine readable instructions, stored in memory 310. Alternatively, all or some of the processes disclosed herein may be stored in one or more memory devices that are part of a computer system that is separate from ultrasound imaging system 300. In the latter case, additional processing hardware may be added to existing ultrasound imaging system 300 to enhance its processing capability for performing processes disclosed herein. One skilled in the art will readily recognize that such variations are possible and within the scope of the invention.

At step 405, ultrasound processor 305 executes instructions to acquire a first ultrasound image and a second ultrasound image from ultrasound probe 100. Ultrasound probe 100 is moved between these image acquisitions—or is moving during these image acquisitions—so that the first ultrasound image corresponds to first field of view 110a, and the second ultrasound image corresponds to second field of view 110b, which are separated by elevation distance $\Delta z$. Ultrasound processor 305 then stores the first and second ultrasound images in memory 310. The desired elevation distance $\Delta z$ may be such that shallow resolution cells 115a and 115b have sufficient overlap so that their computed correlation coefficient $\rho$ is approximately 0.5. This is because, at lower correlation coefficient $\rho$ values, the error in elevation distance $\Delta z$ as a function of correlation coefficient $\rho$ value becomes severe. This will be apparent to one skilled in the art by observing the shape of the correlation curve set 200 of FIG. 2.

At step 410, ultrasound processor 305 executes instructions to divide the first and second ultrasound images into patches, wherein each patch is an aggregate of a predetermined number of pixels in a predetermined geometry.

Figure 5A:
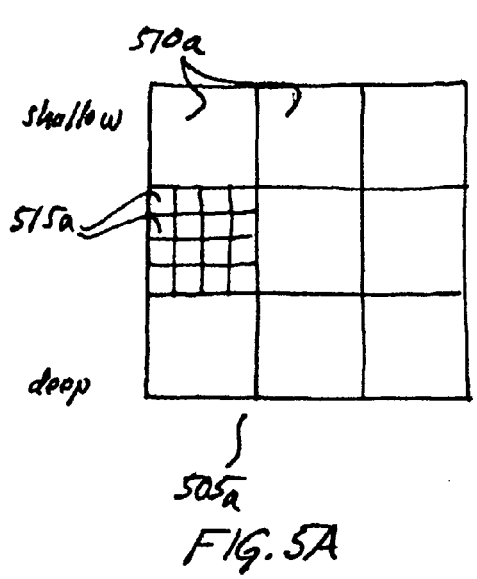
FIG. 5A illustrates an exemplary first ultrasound image, which is divided into patches and sub-patches.
Figure 5B:
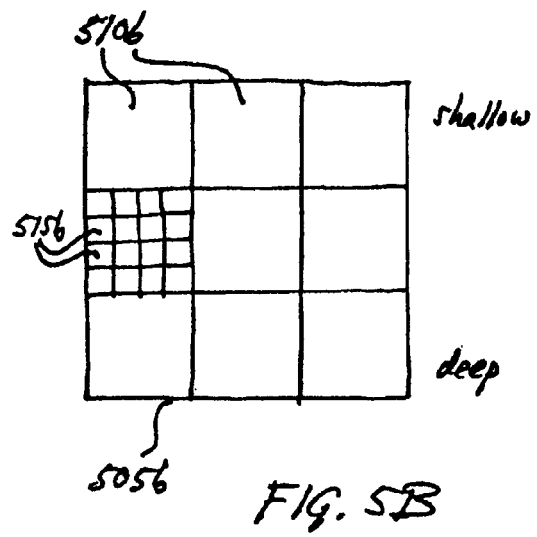
FIG. 5B illustrates an exemplary second ultrasound image, which is divided into patches and sub-patches.

FIG. 5A illustrates an exemplary first ultrasound image 505a, corresponding to first field of view 110a; and FIG. 5B illustrates an exemplary second ultrasound image 505b, corresponding to second field of view 110b. First and second ultrasound images 505a and 505b are each composed of a plurality of pixels (not shown). Each pixel column (for both images) corresponds to a transducer within transducer array 105. Each row of pixels is corresponds to a sample time, as processed by ultrasound probe 100.

As illustrated in FIGS. 5A and 5B, first ultrasound image 505a and second ultrasound image 505b are respectively divided into a plurality of sub-patches 510a and 510b, in accordance with step 410. Each patch 510a and 510b may have, for example, around 4000-5000 pixels, arranged in a square or rectangular geometry. Other pixel quantities are possible. The number of patches, and the number of pixels per patch, may vary, with a tradeoff between processing time and expected anisotropy of the tissue, as well as other factors.

Further to step 410, ultrasound processor 305 may execute instructions to divide each patch 510a and 510b into a plurality of sub-patches 515a and 515b. Each patch 510a and 510b may be divided into, for example, 18 columns and 7 rows of sub-patches 515a and 515b, respectively. Further, each sub-patch 515a and 515b may encompass, for example, around 700 pixels. One skilled in the art will readily appreciate that this configuration is exemplary, and other arrangements and geometries of sub-patches 515a and 515b are possible and within the scope of the invention.

Still further to step 410, ultrasound processor 305 may execute instructions to normalize first ultrasound image 505a by dividing the amplitude of each pixel by the mean amplitude of all of the pixels of first ultrasound image 505a. The same may be done for second ultrasound image 505b.

At step 415, ultrasound processor 305 executes instructions to compute the signal-to-noise ratio and skewness (hereinafter referred to collectively as "R and S") of each patch 505a and 505b. In doing so, ultrasound processor 305 may execute instructions to compute R and S according to the following relations:

$$R = \frac{\langle A^{v_r} \rangle}{\sqrt{\langle A^{2v_r} \rangle - \langle A^{v_r} \rangle}} \equiv \frac{\text{mean}}{\text{variance}}$$

$$S = \frac{\langle (A^{v_s} - \langle A^{v_s} \rangle)^3 \rangle}{(\langle A^{2v_s} \rangle - \langle A^{v_s} \rangle^2)^{\frac{3}{2}}} \equiv \frac{\text{skew}}{\text{variance}}$$

where A is the amplitude of the ultrasound RF envelope within patch 505a or 505b, $v_r$ and $v_s$ are signal powers, and $\langle \ldots \rangle$ denotes the mean. Signal powers may be set so that $v_r = 2v_s = 1$, as an example. Accordingly, ultrasound processor 305 executes instructions to compute R and S for each patch 505a and 505b, and stores the corresponding values in memory 310.

At step 420, ultrasound processor 305 executes instructions to compare the R and S values for each patch 505a and 505b with an FDS discrimination function.

Figure 6:
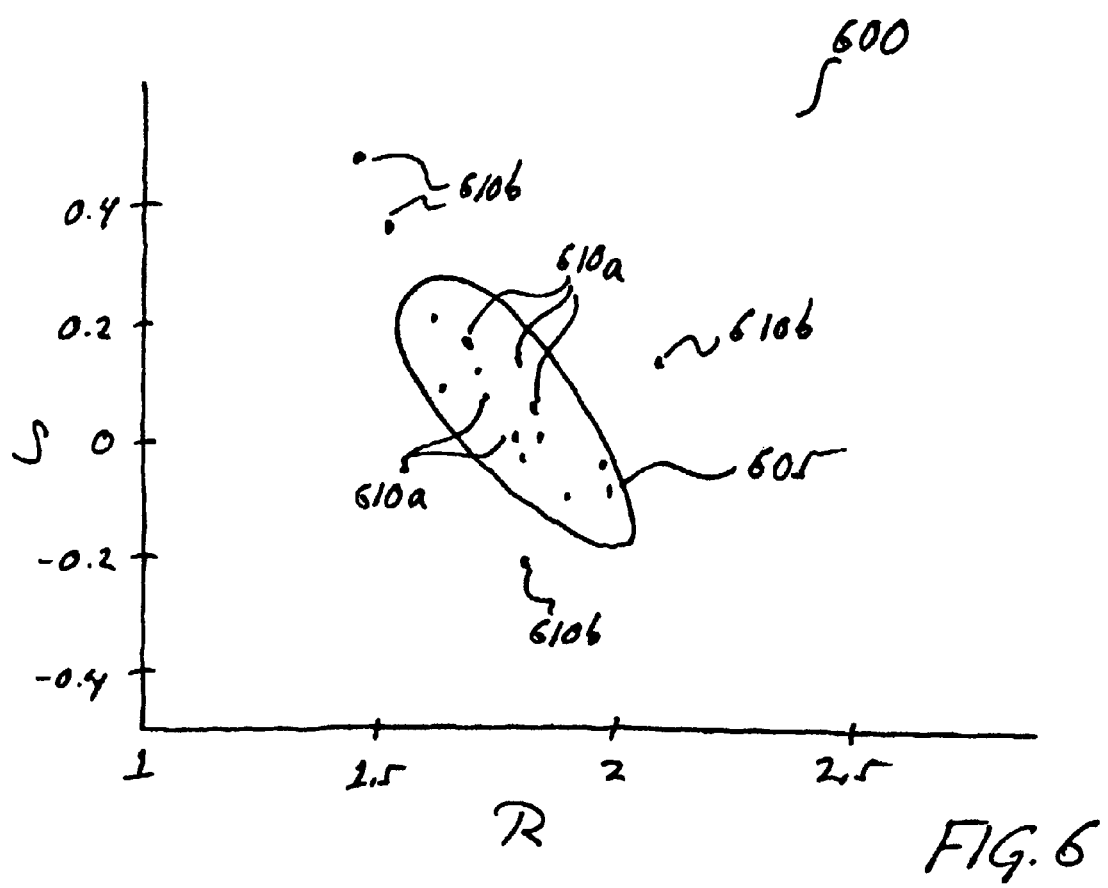
FIG. 6 illustrates an exemplary skewness vs. signal to noise plot corresponding to the patches of FIGS. 5A and 5B.

FIG. 6 illustrates an skewness vs. signal to noise plot (hereinafter S/R plot) 600, which graphically depicts the FDS discrimination function. Also depicted is an FDS patch ellipse 605. FDS patch ellipse 605 is a predetermined R and S parameter space that may graphically plot as an ellipse on S/R plot 600. FDS patch ellipse 605 defines a boundary, or range, of acceptable R and S values, so that R and S values within the FDS patch ellipse correspond to a patch that has speckle scatterers 112 of sufficient quantity and distribution to result in a symmetric Gaussian distribution. In other words, the statistical qualities of the speckle scatterers within a given patch have a sufficient signal to noise ratio and skewness to provide a correlation coefficient $\rho$ of sufficient fidelity to provide an elevation distance $\Delta z$ between first field of view 110a and second field of view 110b. In other words, R and S values 610a are to be considered FDS (fully developed speckle), which may be used to calculate elevation distance $\Delta z$ (i.e., out of plane motion distance). R and S values 610b that lie outside FDS patch ellipse 605 correspond to patches have either an insufficient number of speckle scatterers 112, or that have some structure (e.g., vein or bone), which contaminates the statistical properties of the pixel amplitudes within the patch.

The data values defining FDS patch ellipse 605 may be stored in memory 310, and retrieved by ultrasound processor 305 at step 420. Alternatively, FDS patch ellipse 605 may not exist as a predetermined set of parameters. In this case, ultrasound processor 305 may execute instructions to plot R and S values 610 (610a and 610b are not yet discriminated), and then define a boundary for FDS patch ellipse 605 based on the statistical distribution of the R and S data points. This may be accomplished using known algorithms for removing outliers from data. One skilled in the art would recognize that there exist algorithms for statistically discriminating between R and S values 610a and 610b. Further, as used herein, the term "ellipse" may refer to a boundary of any shape.

Further, although S/R plot 600 is illustrated in FIG. 6 as a visual graph, one skilled in the art will recognize that the data need not be graphically depicted, and that the data may be stored in matrix form in memory 310.

At step 425, ultrasound processor 305 executes instructions to identify "bad" patches, which correspond to R and S data points 610b. In other words, the R and S data points 610b lie outside the FDS patch ellipse 605 and would thus not qualify as FDS. Again, this means that the signal to noise ratio and skewness are such they have a Gaussian distribution of speckle scatterers 112, and thus the plot of correlation coefficient ρ as a function of elevation distance Δz would not conform to a Rayleigh distribution. The corresponding bad patches in first and second ultrasound images 505a and 505b are tagged as bad patches in memory device 310.

At this stage of exemplary process 400, first and second ultrasound images 505a and 505b are respectively divided into patches 510a/510b and sub-patches 515a/515b. For both images 505a and 505b, some of the patches 510a and 510b may have been tagged as bad patches, and some may have been tagged as good patches. Depending on the nature of the tissue medium, and the presence of structure such as vein and bone, it may be the case that all of patches 510a and 510b are tagged as bad patches. The next phase of process 400 may include identifying good and bad sub-patches among sub-patches 515a and 515b.

As described below, steps 430-455 are performed on sub-patches of a given bad patch of one of ultrasound images 505a and 505b. For convenience of description, an example scenario will be described in which the steps are performed on sub-patches 515a of a bad patch 510a of first ultrasound image 505a. However, one skilled in the art will readily recognize that this description may pertain to sub-patches of 515b of a bad patch 510b of second ultrasound image 505b. Further, one skilled in the art will also recognize that steps 430-455 may be performed "simultaneously" on both first and second ultrasound images 505a and 505b in a multi-tasking operating system or parallel processing computer architecture, and that such variations are within the scope of the invention.

At step 430, ultrasound processor 305 executes instructions to compute the R and S values for all of the sub-patches 515a of bad patch 510a, using the mathematical relations shown above for computing R and S values. Ultrasound processor 305 then executes instructions to store these R and S values in memory 310.

At step 435, ultrasound processor 305 executes instructions to compare the R and S data values computed and at step 430 with a sub-patch FDS discrimination function. In doing so, ultrasound processor 305 maps the R and S data values on a sub-patch S/R plot.

Figure 7:
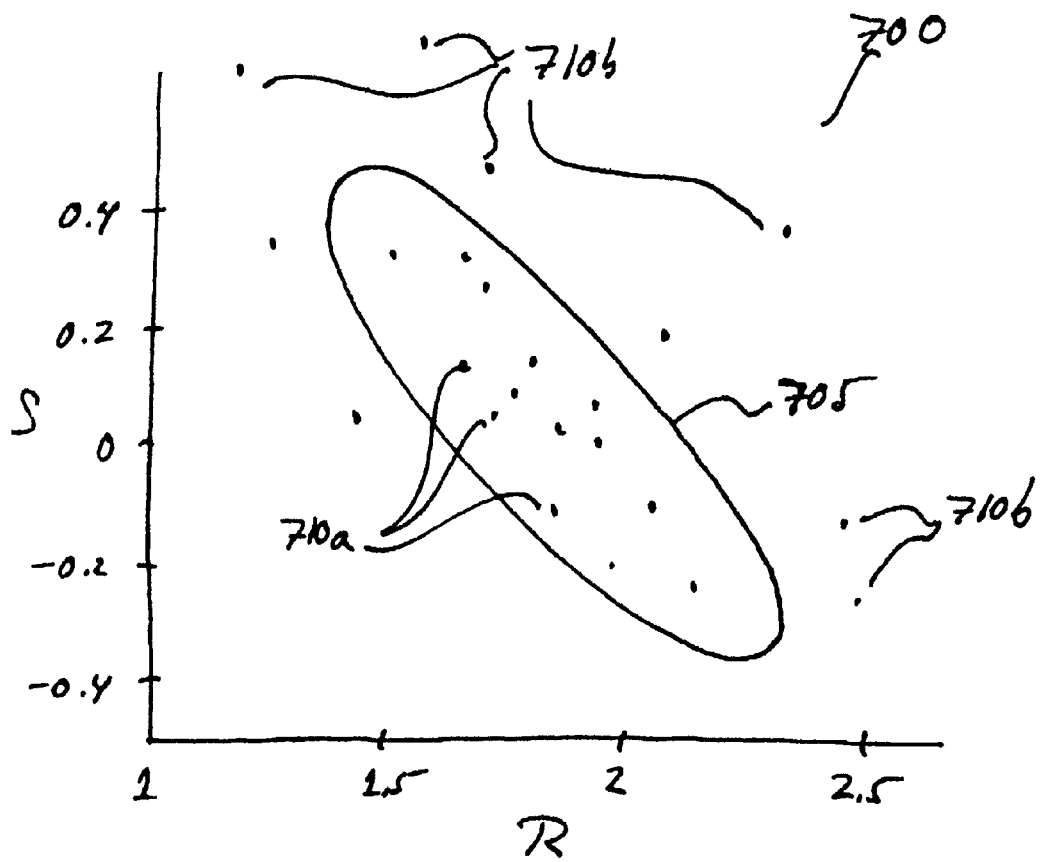
FIG. 7 illustrates an exemplary skewness vs. signal to noise plot corresponding to the sub-patches of FIG. 5C.

FIG. 7 illustrates an exemplary sub-patch S/R plot 700. Sub-patch S/R plot 700 may be similar to S/R plot 600 described above. However, sub-patch S/R plot 700 has the R and S data values 710a and 710b corresponding to sub-patches 515a (as opposed to patches 510a), and an FDS sub-patch ellipse 705 (as opposed to FDS patch ellipse 605). Note that the area of FDS sub-patch ellipse 705 is greater than that of FDS patch ellipse 605. This is due to the fact that each of the sub-patches 515a encompasses fewer speckle scatterers 112 that do the patches 510a. Accordingly, having fewer speckle scatterers 112 means that the statistics will not be as well behaved (in a Gaussian sense) compared to having many more speckle scatterers 112. Further, given the fact that there are fewer speckle scatterers 112 in a given sub-patch 515a, compared to patch 510a, the R and S data points 710a and 710b will generally be more broadly distributed on sub-patch S/R plot 700, compared to R and S data points 610a and 610b of S/R plot 600.

As stated above with regard to S/R plot 600, sub-patch S/R plot 700 need not be implemented as a graphic plot, as illustrated in FIG. 7. It may be an area of computer readable memory in which R and S data points 710a and 710b are mapped, along with parameter data corresponding to FDS sub-patch ellipse 705. In doing so, the R and S data may be mapped into a 2D vector space.

Further to step 435, ultrasound processor 305 executes instructions to discriminate R and S data points between those that lie within FDS sub-patch ellipse 705 (i.e., R and S data points 710a) from those that lie outside FDS sub-patch ellipse 705 (i.e., R and S data points 710b). It may do so, for example, by computing a 2D variable range space corresponding to FDS sub-patch ellipse 705, and then comparing each R and S data point to the variable range space. FDS sub-patch ellipse 705 may exist as a set of predetermined parameter values stored in memory 310. Alternatively, ultrasound processor 305 may execute instructions to estimate an FDS sub-patch ellipse based solely on the R and S data values, using algorithms for identifying outlier data, which are known to the art.

At step 440, ultrasound processor 305 executes instructions to identify "bad" sub-patches, thereby also identifying all of the "good" sub-patches. Bad sub-patches are those whose R and S data points 710b lie outside FDS sub-patch ellipse 705. In doing so, ultrasound processor 305 may execute instructions to assign a flag, or some identifier, to the sub-patches 515a in first ultrasound image 505a having R and S data points 710b.

Figure 5C:
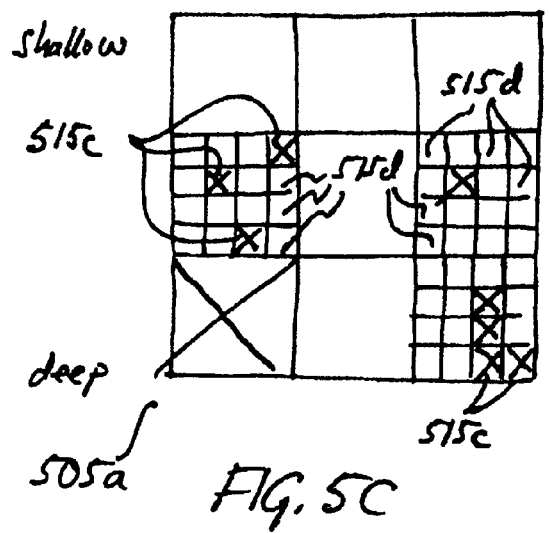
FIG. 5C illustrates an exemplary first ultrasound image, in which bad sub-patches are identified and tagged.

FIG. 5C illustrates first ultrasound image 505a, wherein exemplary bad sub-patches 515c exist among exemplary good sub-patches 515d.

At step 445, ultrasound processor 305 executes instructions to "stitch" together, or aggregate, good sub-patches 515d of the given bad patch 510a. In doing so, ultrasound processor 305 may, for example, execute instructions to map all of the data corresponding to speckle scatterers 112 within the good sub-patches 515d of a given bad patch 510a, identified at step 440 into a single array of data in memory 310.

At step 450, ultrasound processor 305 executes instructions to compute an R and S value for the aggregated good patch resulting from step 445. In doing so, ultrasound processor 305 may execute instructions to compute the R and S value using the mathematical relations for these values described above.

At step 455, ultrasound processor 305 executes instructions to compare the R and S value computed at step 450 with the FDS patch ellipse 605 (see FIG. 6). If the R and S value lie within the FDS patch ellipse 605, then ultrasound processor 305 assigns an identifier to the aggregated good patch. Otherwise, if the R and S value of the aggregated patch lies outside FDS patch ellipse 605, then ultrasound processor 305 assigns an identifier to the aggregated bad patch.

Aggregating the good sub-patches 515d into a single patch (step 445), computing the R and S values (step 450), and comparing the computed R and S value with FDS patch ellipse 605 (step 455) may serve to identify false positives among the sub-patches 515a within patch 510a. In dividing patch 510a into sub-patches 515a, there is the possibility that the smaller sub-patch 515a may completely encompass a tissue structure (e.g., vein or bone) such that the statistics within the sub-patch are well behaved. In other words, even though the sub-patch 515a covers a structure, it does so such that the tissue volume sampled by the corresponding resolution cell is isotropic, even though it may not have any speckle scatterers 112. In this case, the R and S value of that given sub-patch 515a will likely lie within FDS sub-patch ellipse 705 and be identified as a good sub-patch 515d. By recomputing the R and S value for the aggregated sub-patches 515a, the anomalous good sub-patch 515d will thus stand out, because the structure will be statistically revealed in the context of its multiple neighboring good sub-patches 515d. Accordingly, if there is one or more false positives within the aggregated patch, the subsequent computed R and S data will be corrupted, thus likely placing the R and S data outside FDS patch ellipse 605. At the conclusion of step 455, all of the good patches and good aggregated patches may be identified in both first ultrasound image 505a and second ultrasound image 505b.

At step 460, ultrasound processor 305 executes instructions to identify all good patches and good aggregated patches that are common to both first ultrasound image 505a and second ultrasound image 515b. In doing so, ultrasound processor 305 may store identifiers for the corresponding pairs of good patches and good aggregated patches in memory 310. It may be the case that there are few corresponding pairs of good patches and/or good aggregated patches. In general, to determine elevation distance Δz (or out of plane motion) between first field of view 110a and second field of view 110b, it is desired to have at least three corresponding pairs of good patches and/or good aggregated patches.

At step 465, ultrasound processor 305 executes instructions to compute the correlation coefficient for each corresponding pair of good patches and/or good aggregated patches between first ultrasound image 505a and second ultrasound image 505b. Ultrasound processor 305 may do so by computing the following relation for each pair:

$$\rho(W, Z) = \frac{\sum w_i z_i - N\mu_w \mu_z}{\sqrt{(\sum w_i^2 - N\mu_w^2)(\sum z_i^2 - N\mu_z^2)}}$$

where W and Z respectively refer to the good patch (or good aggregate patch) of first ultrasound image 505a and the corresponding good patch (or good aggregate patch) of second ultrasound image 505b, $w_i$ refers to the intensity value of the ith pixel of patch W, $z_i$ refers to the intensity value of the ith pixel of patch Z, $\mu_w$ refers to the mean intensity value for the pixels in patch W, and $\mu_z$ refers to the mean intensity value for the pixels in patch Z. Ultrasound processor 305 then stores the computed correlation coefficients ρ(W,Z) in memory 310.

At step 470, ultrasound processor 305 executes instructions to compute an elevation distance Δz for each correlation coefficient computed at step 465. In doing so, ultrasound processor 305 may execute instructions to retrieve a plurality of correlation curves, each corresponding to an image depth, and the correlation coefficients ρ(W,Z) computed at step 465.

Figure 8:
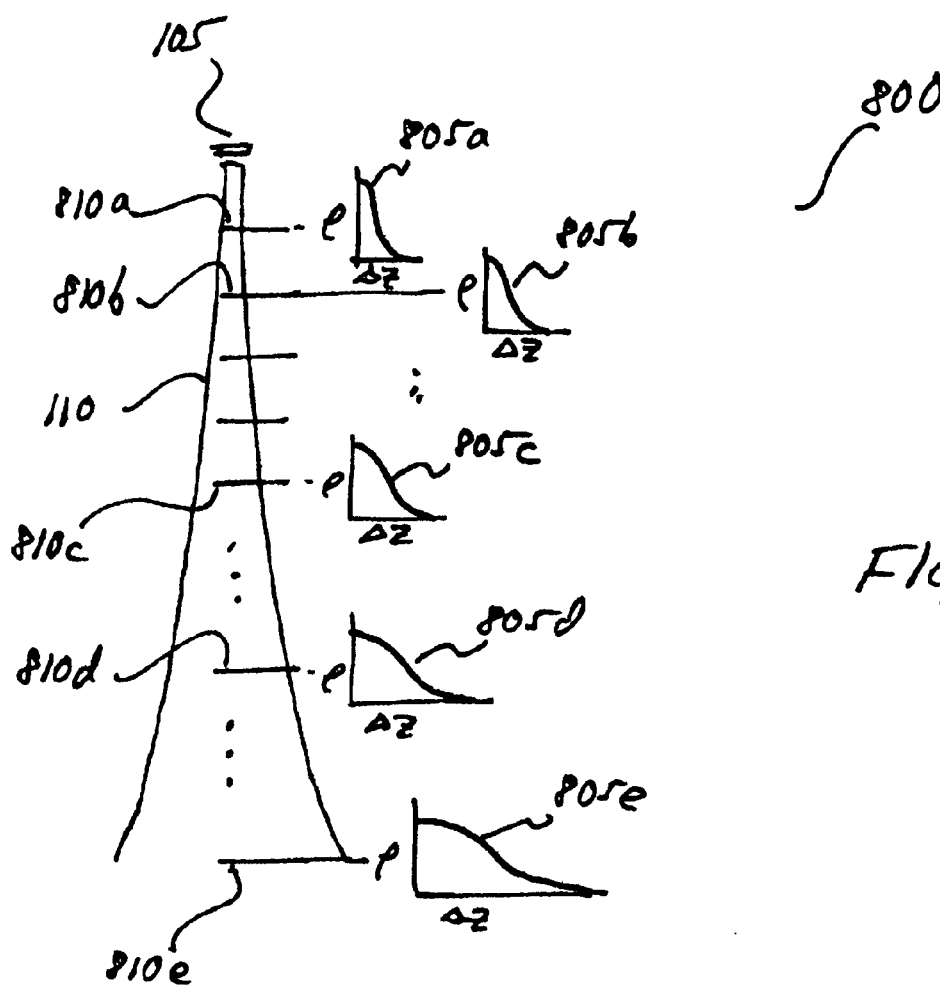
FIG. 8 illustrates an exemplary ultrasound field of view, along with exemplary image depths.

FIG. 8 illustrates an exemplary ultrasound field of view 110, and a plurality of image depths 810a-e. For each image depth 810a-e there is a corresponding correlation curve 805a-e. Each correlation curve 805a-e corresponds to a Rayleigh distribution that correlates a given correlation coefficient ρ with an elevation distance Δz, as discussed above with regard to FIG. 2. The axial spacing of image depths 810a-e may be substantially constant, or may vary. Further, each correlation curve 805a-e may be stored in memory 310 as a look up table, or they may be parametrically defined. One skilled in the art will readily appreciate that such variations to the storing of correlation curves 805a-e are possible and within the scope of the invention.

Further to step 470, ultrasound processor 305 executes instructions to compute the elevation distance Δz from the corresponding correlation coefficients ρ(W,Z). Each corresponding pair of patches (or aggregated sub-patches) W and Z has an associated image depth 810a-e. Accordingly, the result of step 470 is a series of elevation distances Δz as a function of image depth 810a-e.

Figure 9A:
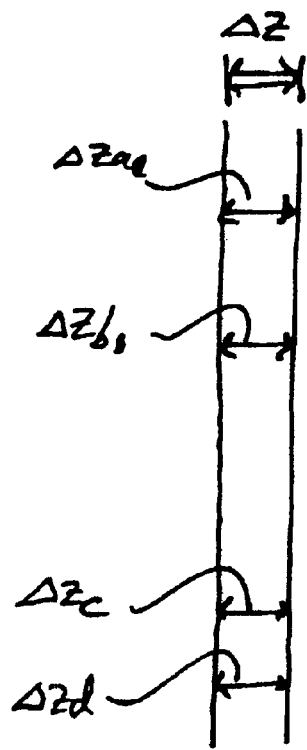
FIG. 9A illustrates an exemplary out of plane translation between two fields of view.
Figure 9B:
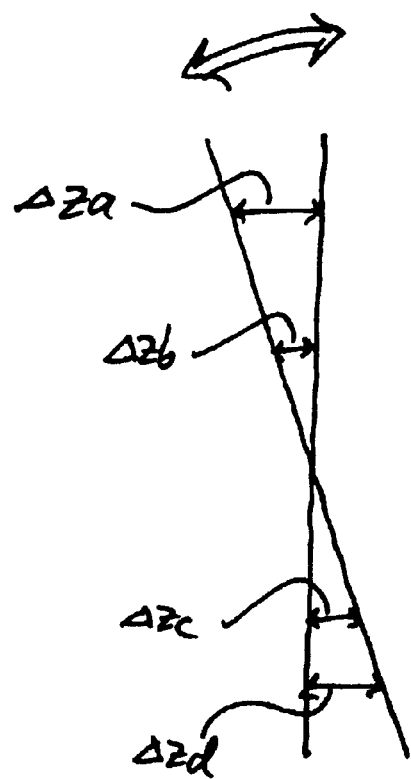
FIG. 9B illustrates an exemplary out of plane rotation between two fields of view.

FIGS. 9A and 9B illustrate two exemplary out of plane motions. FIG. 9A illustrates a translation along elevation distance Δz; and FIG. 9B illustrates a rotation around the lateral or y-axis. In the former case, the elevation distance Δz computed at step 470 may be substantially constant as a function of distance. However, in the latter case, the elevation distance Δz computed at step 470 may vary in amplitude such that the location of the axis of rotation may be identified by the trend in elevation distance Δz as a function of image depth 810a-e. Further, it will be apparent to one skilled in the art that combinations of out of plane translation and rotation are possible, and that computing elevation distance Δz as a function of image depth 810a-e may reconstruct that motion.

At the end of process 400, memory 310 will have stored first and second ultrasound images 505a and 505b, and values for the out of plane motion of ultrasound probe 100 between the acquisition of the two images. By repeating process 400 over a range of out of plane motion of ultrasound probe 100, ultrasound processor 305 may then execute instructions to construct a 3D image of the tissue medium using image processing techniques that are known to the art.

Many variations to process 400 are possible and within the scope of the invention. For example, process 400 may be modified so that patches may be defined that encompass corresponding areas of both first ultrasound image 505a and second ultrasound image 505b.

Figure 10:
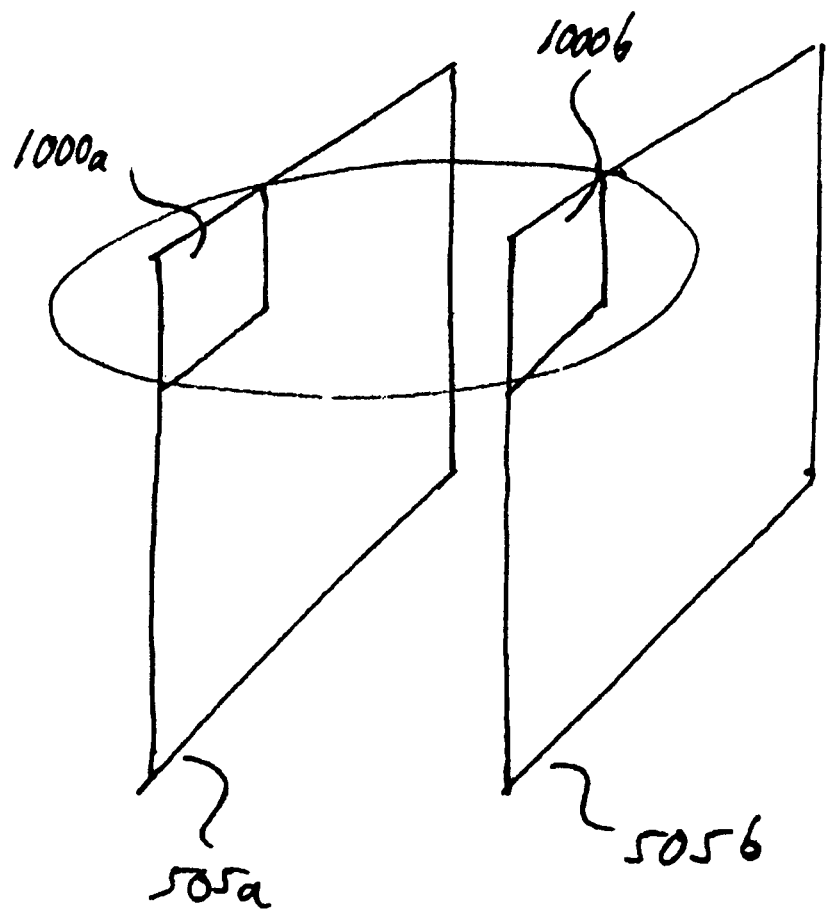
FIG. 10 illustrates an two corresponding patches, each of a different ultrasound image, which are merged into a single patch.

FIG. 10 illustrates such a variation. As illustrated, corresponding patches 1000a and 1000b may be combined. To accomplish this, ultrasound processor 305 may execute instructions to combine the pixel data of patch 1000a and 1000b into a single array of data, and then compute the R and S data of this merged patch at step 415. There may be two advantages in this approach. First, data from a large number of pixels (e.g., 4-5K pixels) may be obtained from a patch that is considerably smaller in each of first and second ultrasound images 505a and 505b. This may lead to using smaller patches, which may increase the likelihood of identifying more good patches, depending on the distribution and size of structure (e.g., vein or bone) in first and second ultrasound images 505a and 505b. Second, merging patches in this manner may obviate the need for step 460, because a given merged patch is formed from corresponding areas of first and second ultrasound images 505a and 505b. As such, a good patch is automatically good for the same area of each image.

In another variation, ultrasound beamsteering may be employed to increase the number of pixels per patch, and thus reduce the size of each patch.

Figure 11:
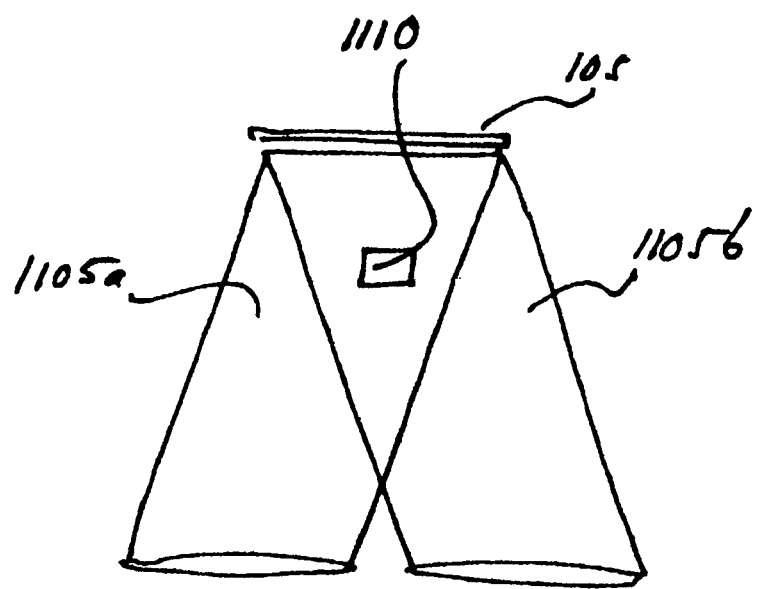
FIG. 11 illustrates two beamsteered ultrasound fields of view and a patch that is imaged by both of these fields of view.

FIG. 11 illustrates two steered ultrasound beams 1105a and 1105b. A given patch 1110 may be defined in an overlap region between ultrasound beams 1105a and 1105b. Ultrasound beamsteering, in which the differential phasing is applied to clusters of transducers within transducer array 105, is known to the art. By employing two steered ultrasound beams 1105a and 1105b to image the same patch 1110, twice the number of pixels may be obtained from a single volume of tissue medium. This may increase the fidelity of the R and S values computed for each patch 1110. It may also reduce the size of a given patch, which may increase the number of good patches and improve the quality of the computation of out of plane motion by having more good patches (and thus more elevation distance $\Delta z$ data points). One skilled in the art will recognize that such variations to process 400 are possible and within the scope of the invention.

Further to this variation, in addition to (or alternative to) acquiring multiple images using beamsteering, process 400 may vary other ultrasound imaging parameters in imaging a single patch. For example, instead of imaging a single patch using two different beamsteered fields of view, ultrasound probe 100 may be configured to acquire multiple images of a single patch using different frequencies, or different ultrasound focusing modes that are known to the art.

Figure 12:
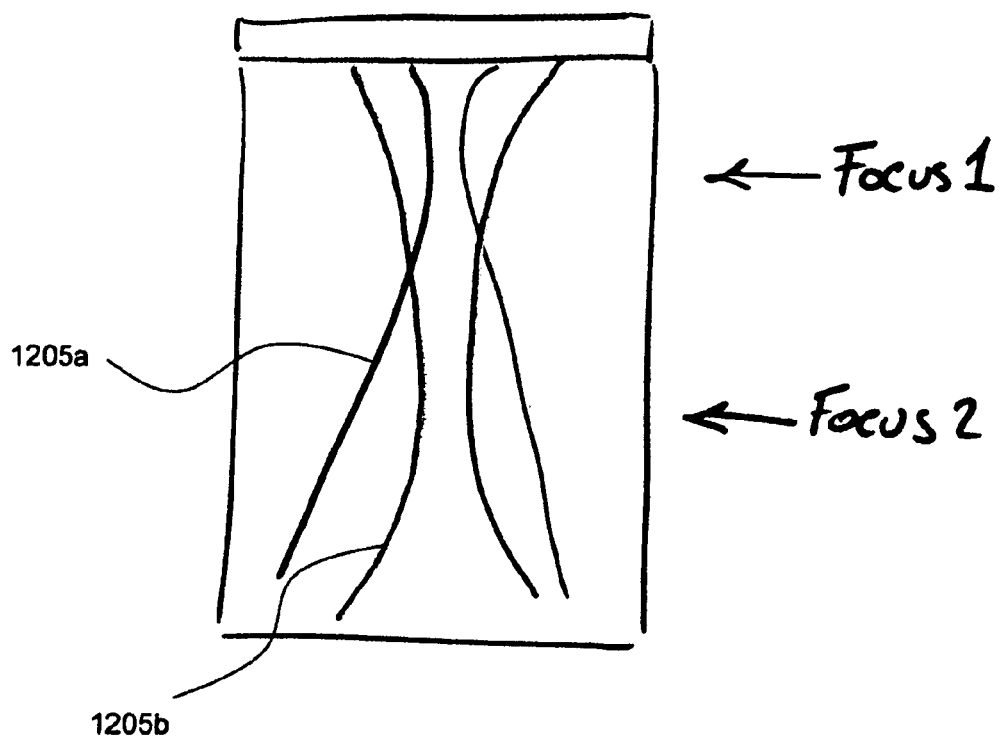
FIG. 12 illustrates two ultrasound fields of view that are acquired using different focusing modes.

FIG. 12 illustrates two ultrasound images 1205a and 1205b, whereby each image is acquired using different focusing modes. By using multiple frequencies and/or multiple focusing modes, more independent pixel data may be acquired for a single patch. This may increase the number of pixels for a given patch, and thus improve the statistical qualities of the later-computed R and S data, but it may also allow for a smaller patch to be used.

In another variation of process 400, FDS patch ellipse 605 and FDS sub-patch ellipse 705 may not be implemented as hard boundaries, but may be implemented in gradations from an FDS ellipse centroid. In this case, R and S data points closer to the centroid of the FDS ellipse may be given a higher weight than those further from the centroid. In this case, the patches or sub-patches corresponding to R and S values closer to the centroid may be given a higher weight in computing out of plane motion.

The plurality of correlation curves 805a-e may be predetermined in a calibration procedure using an isotropic tissue simulating phantom, which are known to the art. Phantom-based calibration may be done by acquiring ultrasound data of a phantom is a succession of images, each spaced apart by a controlled elevation distance $\Delta z$. Once ultrasound images are collected for a sequence of elevation distances $\Delta z$, correlation coefficients $\rho$ may be computed for each elevation distance $\Delta z$, and then stored in a look up table in memory 310. Alternatively, as stated above, the set of correlation coefficients $\rho$ may also be computed and stored parametrically, to be later used at step 465 of process 400.

An alternate, or supplemental calibration procedure may be done using a tissue sample instead of a phantom. In this case, ultrasound images may be acquired while ultrasound probe 100 is moved in a controlled fashion over a range of elevation distances $\Delta z$, similar to phantom-based calibration. Once the ultrasound image data is acquired and stored, ultrasound processor 305 may execute instructions to perform steps 405-465 of process 400. The result is an array of correlation coefficients $\rho$ as a function of elevation distance $\Delta z$. In this case, instead of computing elevation distance $\Delta z$, which is known, ultrasound processor 305 executes instructions to store the computed correlation coefficients $\rho$ as a function of elevation distance $\Delta z$. Depending on the size and distribution of structure in the tissue medium, the computed correlation coefficients $\rho$ may compared with stored correlation coefficients $\rho$ from previous calibrations. This may be useful for verifying or refining previous calibrations.

Another variation to process 400 may include a parallel image processing path (not shown), in which a structure having a known shape may be identified in the first and second ultrasound image and used as a fiducial marker for providing additional elevation distance $\Delta z$. This additional elevation distance $\Delta z$ may be used to more optimally reconstruct a 3D ultrasound image from first and second ultrasound images 505a and 505b. This may be useful in two exemplary scenarios: one involving an imaged surgical device, and another involving a pre-imaged anatomical structure of known shape.

Figure 13:
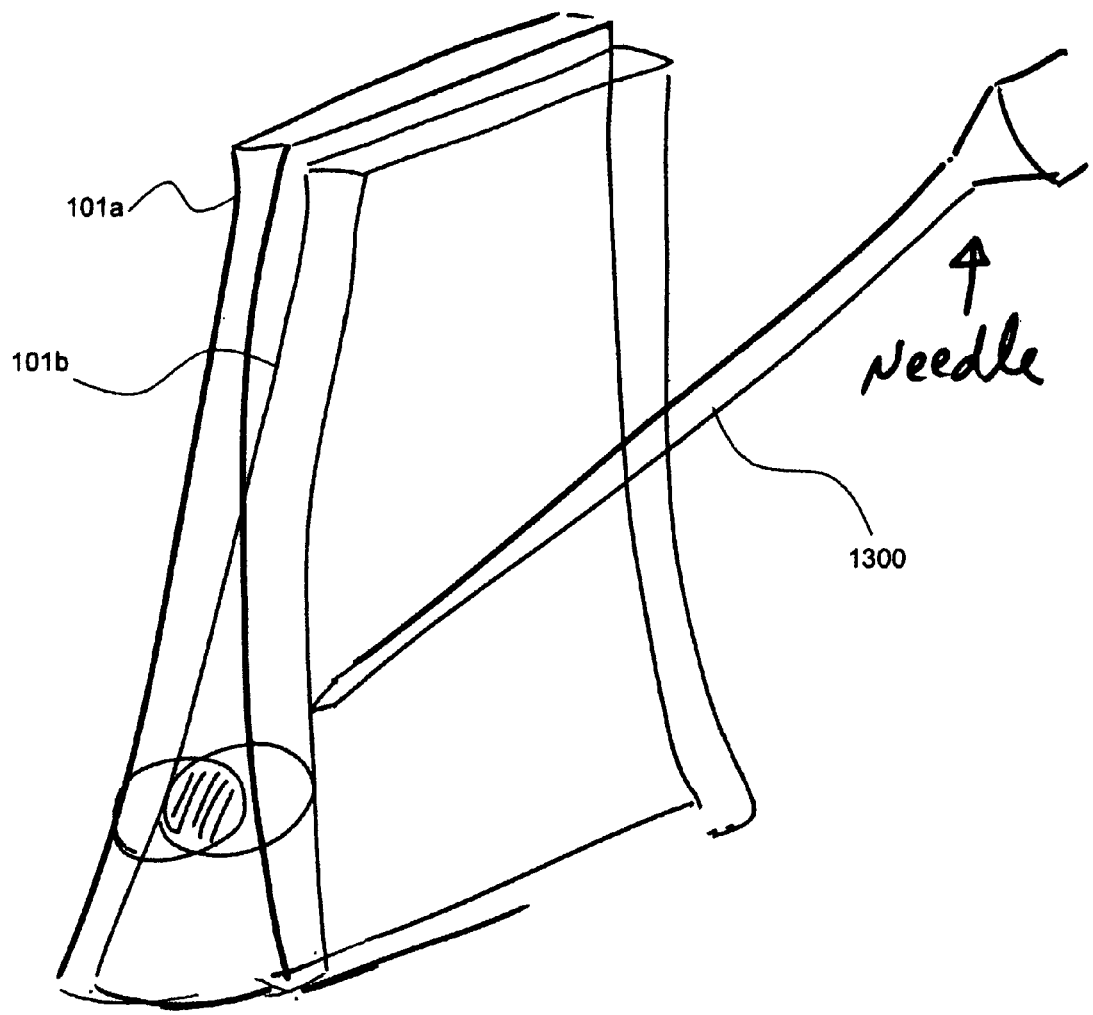
FIG. 13 illustrates two ultrasound fields of view imaging a structure of known shape, wherein the structure is a surgical device.

FIG. 13 illustrates first and second fields of view 110a and 110b, along with surgical device 1305. Surgical device 1305, such as a needle, may be inserted into the tissue medium imaged by ultrasound probe 100. This may be done in situations in which ultrasound imagery is used to help guide or track the surgical device. In this case, the shape of surgical device 1305 is known. Accordingly, if the reconstruction of 3D ultrasound imagery, including first and second ultrasound images 505a and 505b, results in a 3D image in which surgical device 1305 does not appear as it is known to appear, ultrasound processor 305 may execute instructions to further adjust the relative orientation and position of ultrasound image 505a and 505b so that the image of the surgical device more closely resembles its known shape. This exemplary scenario may be done in biopsy procedures, ablative therapy procedures, or other surgical procedures in which real time 3D imaging of a target tissue medium is desired. Ultrasound processor 305 may execute instructions to recognize, or segment, surgical device 1305 according to image processing algorithms that are known to the art.

Figure 14:
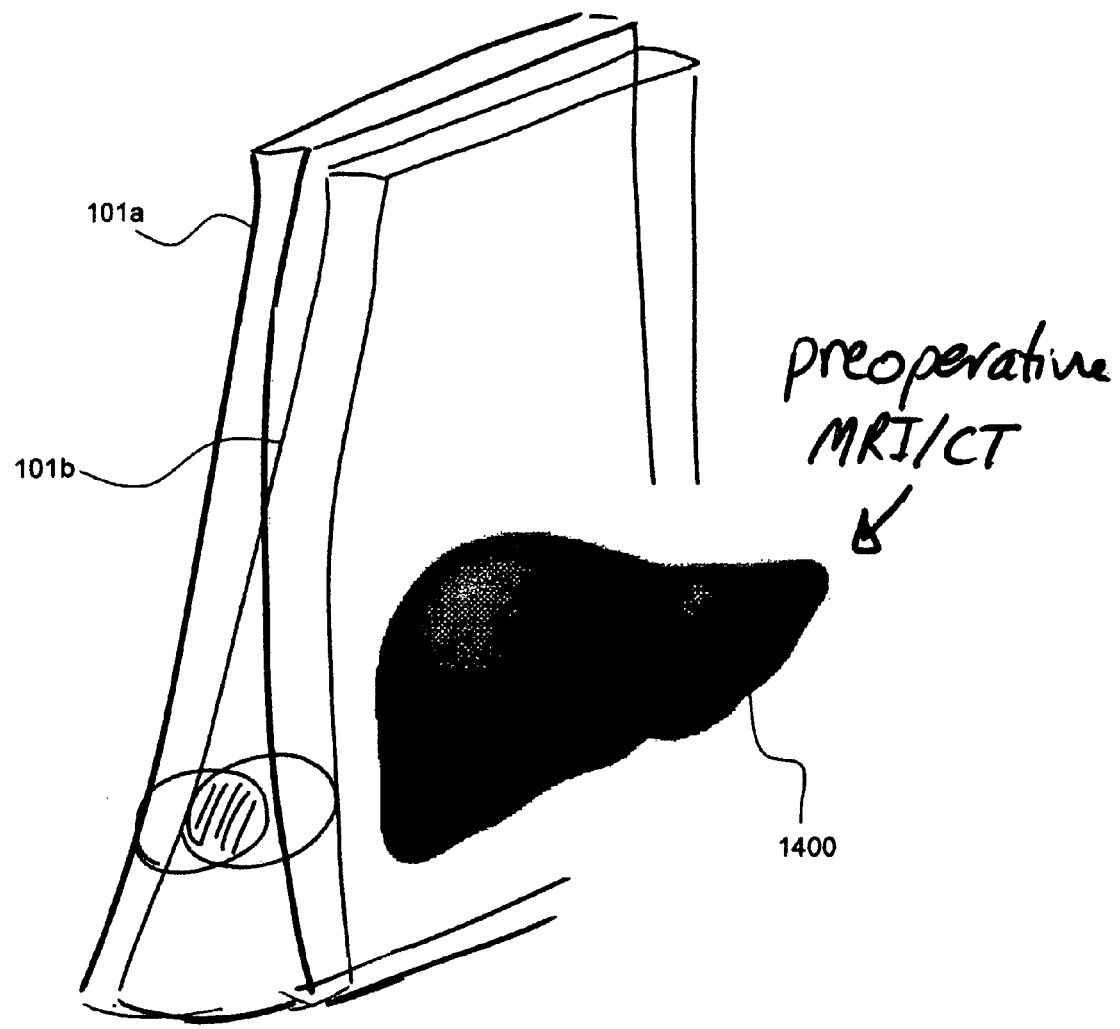
FIG. 14 illustrates two ultrasound fields of view imaging a structure of known shape, wherein the structure is a previously-imaged anatomical feature.

FIG. 14 illustrates first and second fields of view 110a and 110b, and a known anatomical structure 1405. In this exemplary scenario, the tissue medium may have been previously imaged using a 3D imaging modality, such as MRI or CT. In this case, the 3D image may include anatomical structure 1405 that will not likely have changed shape since the 3D image was acquired. In this scenario, the 3D image that is reconstructed according to the present invention (which includes ultrasound images 505a and 505b) may be adjusted so that the reconstructed 3D ultrasound image of anatomical structure 1405 more closely resembles that imaged previously. In either of these scenarios, ultrasound processor 305 may execute instructions according to image processing techniques that are known to the art for the purposes of manipulating 3D images to account for the configuration of fiducials common to the images.

In another variation of process 400, ultrasound processor 305 may (once a plurality of elevation distances $\Delta z$ have been computed) execute instructions to fit a plane corresponding to the plurality of elevation distances. Referring to FIGS. 9A and 9B, the plane to be fitted to the plurality of elevation distances $\Delta z$ may be considered one of the planes illustrated. It may be the case that some of the plurality of elevation distances $\Delta z$ may be statistically better than others. For example, $\Delta z_b$ may be inordinately longer or shorter that the other $\Delta z$ values. In this case, $\Delta z_b$ would be considered an outlier, and could thus be discarded. Accordingly, process 400 may include a step whereby ultrasound processor 305 executes instructions to fit a rigid plane to the plurality of $\Delta z$ values computed at step 470, compute the errors corresponding to each $\Delta z$ (i.e., the distance between each $\Delta z$ and the rigid plane), and reject the $\Delta z$ values that have an error greater than some threshold.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for generating 3D ultrasound imagery, comprising:
   acquiring a first ultrasound image and a second ultrasound image, the first ultrasound image corresponding to a first image location, and the second ultrasound image corresponding to a second image location, and wherein the first image location and the second image location are separated by an elevation distance;
   dividing the first ultrasound image and the second ultrasound image into a plurality of patches;
   computing a signal to noise ratio value and a skewness value for each of the plurality of patches as statistical parameters that characterize a statistical distribution of speckle scattering within each of the plurality of patches;
   comparing the signal to noise ratio value and skewness value for each patch to a range of acceptable signal to noise ratio values and a range of acceptable skewness values;
   determining whether each patch of the plurality of patches is a good patch, wherein each good patch has a corresponding signal to noise ratio value and skewness value that lie within the range of acceptable signal to noise ratio values and skewness values;
   computing a correlation coefficient for a corresponding pair of good patches, wherein one of the corresponding pair is from the first ultrasound image, and the other of the corresponding pair is from the second ultrasound image; and
   computing an elevation distance corresponding to the correlation coefficient.

2. The method of claim 1, further comprising:
   identifying a plurality of bad patches, wherein the bad patches have a corresponding signal to noise ratio value and skewness value that lie outside the range of acceptable signal to noise values and skewness values;
   dividing each of the bad patches into a plurality of sub-patches; computing a sub-patch signal to noise ratio value and skewness value corresponding to each sub-patch within a bad patch;
   identifying a plurality of good sub-patches, wherein the good sub-patches have a signal to noise ratio value and a skewness value that lie within a range of acceptable signal to noise and skewness values;
   computing an aggregate signal to noise ratio value and skewness value corresponding to the plurality of good sub-patches;
   comparing the aggregate signal to noise ratio value and skewness value to the range of acceptable signal to noise values and skewness values;
   computing an aggregate correlation coefficient for corresponding pluralities of good patches between the first ultrasound image and the second ultrasound image;
   computing an elevation distance corresponding to the aggregate correlation coefficient; and
   constructing a 3D image using the first and second ultrasound images and the elevation distance.

3. The method of claim 1, wherein comparing the signal to noise ratio value and skewness value for each patch to a range of acceptable signal to noise ratio values and a range of acceptable skewness values comprises:
   mapping the signal to noise ratio value and skewness value as a data point in a 2D vector space;
   mapping a Fully-Developed-Speckle ellipse in the 2D vector space; and determining if the data point lies inside the Fully-Developed-Speckle ellipse.

4. The method of claim 1, wherein comparing the signal to noise values and skewness value for each patch to a range of acceptable signal to noise ratio values and a range of acceptable skewness values comprises:
   mapping the signal to noise ratio value and skewness value as a data point in a 2D vector space;
   computing a distance of data point to a centroid corresponding to a Fully-Developed-Speckle ellipse; and
   assigning a weight value to the data point.

5. The method of claim 1, wherein computing the elevation distance comprises applying the correlation coefficient to a correlation curve.

6. The method of claim 5, wherein the correlation curve is one of a plurality of correlation curves, and wherein each of the correlation curves corresponds to a tissue depth.

7. A method for determining out of plane motion between a first ultrasound image and a second ultrasound image; comprising:
   dividing the first ultrasound image into a first plurality of patches, wherein each of the first plurality of patches has a first plurality of pixel data;
   dividing the second ultrasound image into a second plurality of patches, wherein each of the second plurality of patches has a second plurality of pixel data;
   combining one of the first plurality of pixel data with a corresponding one of the second pixel data;
   computing a signal to noise ratio value and a skewness value as statistical parameters corresponding to the combined pixel data;
   comparing the signal to noise ratio value and skewness value with a range of acceptable signal to noise ratio values and skewness values;
   depending on a result of the comparing, computing a correlation coefficient corresponding to the one of the first plurality of pixel data with the corresponding one of the second pixel data;
   computing an elevation distance corresponding to the correlation coefficient; and
   constructing a 3D image using the first ultrasound image, the second ultrasound image, and the elevation distance.

8. The method of claim 7, wherein the first ultrasound image comprises a first beamsteered image and a second beamsteered image, and wherein the first beamsteered image and the second beamsteered image have an overlapping region.

9. The method of claim 8, wherein comparing the signal to noise ratio value and a skewness value with a range of acceptable signal to noise values and skewness values comprises:
   mapping the signal to noise ratio value and skewness value as a data point in a 2D vector space;
   mapping a Fully-Developed-Speckle ellipse in the 2D vector space; and
   determining if the data point lies inside the Fully-Developed-Speckle ellipse.

10. The method of claim 8, wherein computing the elevation distance comprises applying the correlation coefficient to a correlation curve, wherein the correlation curve is one of a plurality of correlation curves, and wherein each of the plurality of correlation curves corresponds to a tissue depth.

11. A system for generating 3D ultrasound images, comprising:
an ultrasound probe;
a processor coupled to the ultrasound probe; and
a memory coupled to the processor,
wherein the memory is encoded with instructions for acquiring a first ultrasound image and a second ultrasound image, the first ultrasound image corresponding to a first image location, and second ultrasound image corresponding to a second image location, and wherein the first image location and the second image location are separated by an elevation distance;
dividing the first ultrasound image and the second ultrasound image into a plurality of patches;
computing a signal to noise ratio value and a skewness value for each of the plurality of patches as statistical parameters that characterize a statistical distribution of speckle scattering within each of the plurality of patches;
comparing the signal to noise ratio value and skewness value for each patch to a range of acceptable signal to noise ratio values and a range of acceptable skewness values;
determining whether each patch of the plurality of patches is a good patch, wherein each good patch has a corresponding signal to noise ratio value and skewness value that lie within the range of acceptable signal to noise ratio values and skewness values;
computing a correlation coefficient for a corresponding pair of good patches, wherein one of the corresponding pair is from the first ultrasound image, and the other of the corresponding pair is from the second ultrasound image; and
computing an elevation distance corresponding to the correlation coefficient.

12. The system of claim 11, further comprising an optical tracking sensor disposed on the ultrasound probe and coupled to the processor.

13. The system of claim 11, wherein the memory is further encoded with instructions for identifying a plurality of bad patches, wherein the bad patches have a corresponding signal to noise ratio value and skewness value that lie outside the range of acceptable signal to noise values and skewness values; dividing each of the bad patches into a plurality of sub-patches; computing a sub-patch signal to noise ratio value and skewness value corresponding to each sub-patch within a bad patch; identifying a plurality of good sub-patches, wherein the good sub-patches have a signal to noise ratio value and a skewness value that lie within a range of acceptable signal to noise and skewness values; computing an aggregate signal to noise ratio value and skewness value corresponding to the plurality of good sub-patches; comparing the aggregate signal to noise ratio value and skewness value to the range of acceptable signal to noise values and skewness values; computing an aggregate correlation coefficient for corresponding pluralities of good patches between the first ultrasound image and the second ultrasound image; and computing an elevation distance corresponding to the aggregate correlation coefficient.

14. The system of claim 11, wherein the instructions for comparing the signal to noise ratio value and skewness value for each patch to a range of acceptable signal to noise ratio values and a range of acceptable skewness values include instructions for:
mapping the signal to noise ratio value and skewness value as a data point in a 2D vector space;
mapping a Fully-Developed-Speckle ellipse in the 2D vector space; and
determining if the data point lies inside the Fully-Developed-Speckle ellipse.

15. A system for generating 3D ultrasound images, comprising:
an ultrasound probe; a processor coupled to the ultrasound probe; and
a memory coupled to the processor, wherein the memory is encoded with instructions for acquiring a first ultrasound image and a second ultrasound image; dividing the first ultrasound image into a first plurality of patches, wherein each of the first plurality of patches has a first plurality of pixel data; dividing the second ultrasound image into a second plurality of patches, wherein each of the second plurality of patches has a second plurality of pixel data; combining one of the first plurality of pixel data with a corresponding one of the second pixel data; computing a signal to noise ratio value and a skewness value corresponding to the combined pixel data; comparing the signal to noise ratio value and skewness value with a range of acceptable signal to noise ratio values and skewness values; depending on a result of the comparing, computing a correlation coefficient corresponding to the one of one of the first plurality of pixel data with the corresponding one of the second pixel data; computing an elevation distance corresponding to the correlation coefficient; and constructing a 3D image using the first ultrasound image, the second ultrasound image, and the elevation distance.

16. The system of claim 15, wherein the instructions for comparing the signal to noise ratio value and a skewness value with a range of acceptable signal to noise values and skewness values includes instructions for:
mapping the signal to noise ratio value and skewness value as a data point in a 2D vector space;
mapping a Fully-Developed-Speckle ellipse in the 2D vector space; and
determining if the data point lies inside the Fully-Developed-Speckle ellipse.

17. The system of claim 16, wherein the instructions for computing the elevation distance include instructions for applying the correlation coefficient to a correlation curve, wherein the correlation curve is one of a plurality of correlation curves, and wherein each of the plurality of correlation curves corresponds to a tissue depth.

18. The system of claim 15, wherein the memory is further encoded with instructions for identifying an imaged surgical device in the 3D image, comparing the imaged surgical device with a known surgical device shape, and adjusting the 3D image to conform the imaged surgical device with the known surgical device shape.

19. The system of claim 15, wherein the memory is further encoded with instructions for identifying an imaged anatomical structure in the 3D image, comparing the imaged anatomical structure with a known anatomical structure shape, and adjusting the 3D image to conform the imaged anatomical structure with the known anatomical structure shape.

20. The system of claim 15, wherein the memory is further encoded with instructions for fitting a plane to the elevation distance, computing an error corresponding to the elevation distance, and disregarding the elevation distance if the error is greater than a threshold.

* * * * *